(12) United States Patent
Metzger et al.

(10) Patent No.: US 9,913,465 B2
(45) Date of Patent: Mar. 13, 2018

(54) WEARABLE AND RE-SEALABLE AROMATIC DEVICE

(71) Applicant: Adeco International LLC, White Plains, NY (US)

(72) Inventors: Gary Metzger, Centerport, NY (US); Clive Li, Brooklyn, NY (US)

(73) Assignee: Adeco Int'l, LLC, White Plains, NY (US)

( * ) Notice: Subject to any disclaimer, the term of this patent is extended or adjusted under 35 U.S.C. 154(b) by 23 days.

(21) Appl. No.: 14/950,793

(22) Filed: Nov. 24, 2015

(65) Prior Publication Data

US 2016/0174694 A1    Jun. 23, 2016

Related U.S. Application Data

(60) Provisional application No. 62/083,389, filed on Nov. 24, 2014.

(51) Int. Cl.

| *A45F 5/00* | (2006.01) |
|---|---|
| *A01M 29/12* | (2011.01) |
| *A61L 9/20* | (2006.01) |
| *A44C 5/00* | (2006.01) |
| *A44C 15/00* | (2006.01) |

(52) U.S. Cl.
CPC ........... *A01M 29/12* (2013.01); *A44C 5/0038* (2013.01); *A61L 9/20* (2013.01); *A44C 15/002* (2013.01); *A45F 2005/008* (2013.01); *A45F 2200/05* (2013.01)

(58) Field of Classification Search
CPC ... A01M 29/12; A01M 1/2061; A44C 5/0038; A44C 15/002; A45F 2200/05; A45F 2005/008; A01K 27/00; A45C 2011/007; A61L 9/20
USPC ........................................................ 224/191
See application file for complete search history.

(56) References Cited

U.S. PATENT DOCUMENTS

| 1,732,028 | A | * | 10/1929 | Reiner | ................ | A01M 1/2044 |
|---|---|---|---|---|---|---|
| | | | | | | 119/654 |
| 3,739,740 | A | | 6/1973 | Fromer | | |
| 4,452,052 | A | * | 6/1984 | Hodge | .................... | A44C 7/00 |
| | | | | | | 63/1.15 |
| 4,483,626 | A | | 11/1984 | Noble | | |
| 5,020,037 | A | | 5/1991 | Raven | | |

(Continued)

OTHER PUBLICATIONS www.pocketbands.com.

(Continued)

*Primary Examiner* — Nathan J Newhouse
*Assistant Examiner* — Matthew Theis
(74) *Attorney, Agent, or Firm* — Morgan Malino (57) ABSTRACT

A wearable aromatic device that can be opened and closed, depending on whether the user wants the device to emit aromas. Aromatics include any substances that are dispersed into the air, regardless of whether they are detectable by humans. Placing an aromatic into a substantially airtight chamber allows the user to allow the device to emit aromas only when desired. A resealable lid can be placed in an open position when aromas are desired, or a close position when they are not. The device is wearable in that it can be worn with a wristband, a pet collar, a belt clip, or any other suitable wearable assembly.

7 Claims, 7 Drawing Sheets

(56) References Cited

U.S. PATENT DOCUMENTS

| | | | |
|---|---|---|---|
| 5,183,171 A * | 2/1993 | Pherigo | B65D 47/0847 |
| | | | 215/232 |
| 5,802,014 A | 9/1998 | Danko | |
| 6,079,872 A | 6/2000 | Besson | |
| 6,244,518 B1 * | 6/2001 | Pogue | A01M 29/12 |
| | | | 215/204 |
| 6,301,196 B1 | 10/2001 | Daniel | |
| 6,340,242 B1 | 1/2002 | Sandidge | |
| 6,464,389 B1 | 10/2002 | Ghoorahoo | |
| 7,316,332 B2 * | 1/2008 | Powers | A45D 34/00 |
| | | | 222/1 |
| D565,828 S | 4/2008 | Page | |
| 7,537,141 B1 * | 5/2009 | Robinson | B65D 47/147 |
| | | | 222/543 |
| 9,427,487 B1 * | 8/2016 | Forbes | A61L 9/12 |
| 2008/0257918 A1 * | 10/2008 | Vogel | B65D 47/0895 |
| | | | 222/480 |
| 2009/0260393 A1 * | 10/2009 | Robbins-Sullivan | A44C 7/00 |
| | | | 63/1.15 |
| 2011/0139823 A1 | 6/2011 | Staudt | |
| 2011/0167536 A1 | 7/2011 | Kellerhals | |
| 2013/0174320 A1 | 7/2013 | Moye | |
| 2015/0352241 A1 * | 12/2015 | Furner | A61L 9/122 |
| | | | 422/105 |

OTHER PUBLICATIONS www.beatfirst.com.
www.amazon.com/gp/product/B00HZO4LRW/ref=pd_lpo_sbs_dp_ss_1.
www.amazon.com/Beilus-Repelient-University-Water-proof-Adjustable/dp/B0051GFCBK.

\* cited by examiner

WEARABLE AND RE-SEALABLE AROMATIC DEVICE

CROSS REFERENCE TO RELATED APPLICATIONS

This application claims the benefit of U.S. Provisional Patent Application Ser. No. 62/083,389, filed Nov. 24, 2014, the disclosure of which is incorporated herein by reference in its entirety for all purposes.

FIELD OF THE INVENTION

The present invention relates to wearable devices that emit aromas.

BRIEF DISCUSSION OF RELATED ART

Small items, such as key and flash drives, are often kept in pockets, wallets, or purses. It is common to occasionally find oneself in a situation where these storage choices are not easily available. For example, athletes, such as runners or swimmers, are required to leave their personal items including wallet and purses in a locker. Some of the small items must be carried around such as prescribed medications for patients for emergency use. Traditionally patients were asked to carry large bottles, loose pills, or blister packs with them in order to process the medication when needed.

Wearable storage device were developed that could be kept within reachable area of a body. For example, U.S. Patent No. US20130174320A1 disclosed a wristband with a concealed key pocket. U.S. Pat. No. 565,828S1, and No. US20110167536A1 disclosed sports wristband with a zipper pocket and sports wristband with layered transparent pockets respectively. U.S. Pat. No. 6,079,872 disclosed a watch casing capable of containing an object such as a cigar cutter.

Numerous patents disclosed wearable storage devices specifically designed for medical application. Some of these patents included an alarm clock to remind the user when to take the medication. U.S. Pat. No. 3,739,740 disclosed a wristband mounted timing pillbox. U.S. Pat. No. 4,483,626 disclosed a medication timing and dispersing apparatus. U.S. Pat. No. 5,802,014 disclosed a strap-on tablet dispersing system includes a system unit which provides timing and alarm functions. U.S. Pat. No. 6,301,196B1 disclosed a compact medication-dispersing unit with a multiple alarm timepiece. U.S. Pat. No. 6,340,242 disclosed a strap-on storage, reminder and watch device. U.S. Pat. No. 6,464,389 disclosed a combined watch and storage container. U.S. Pat. No. 20110139823A1 disclosed a wristband for dispersing a solution in gelation, foam, or liquid form.

While numerous patents on the wearable storage devices are published, none of them are constructed to be significantly difficult for children to open and not difficult for adults or elderly to open. Other non-wearable devices, such as U.S. Pat. No. 5,020,037 (disclosing an alarm pill box in which the alarm can be cancelled by the opening of the lid), mentioned that the lid for the alarm pill box is preferable to be strongly resiliently urged toward its closed position and if necessary, latching or locking to make the lid "child-proof." The disclosures of all the aforementioned applications and patents described in this section are incorporated herein by reference in their entireties for all purposes.

Numerous commercially available wearable storage devices are in the market. Examples are PocketBands, a wristband with a hidden pocket, BeatFirst, a wristband that stores medication, Nitro Pill Case, a small pill case that connects to a necklace, Bellus Mosquito Repellent Wristband, a wristband that carries mosquito repellent. The Bellus Mosquito Repellent Wristband has a sealed container that allows a user to irreversibly punch holes on the top of the container so that the mosquito repellent can be released.

BRIEF DESCRIPTION OF THE DRAWINGS

Various embodiments of the invention are disclosed in the following detailed description and the accompanying drawings.

DETAILED DESCRIPTION

The exemplary embodiments of the present invention are described and illustrated below to encompass methods, systems, and devices related to re-sealable wearable devices for fragrance or insect repellant. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1A:
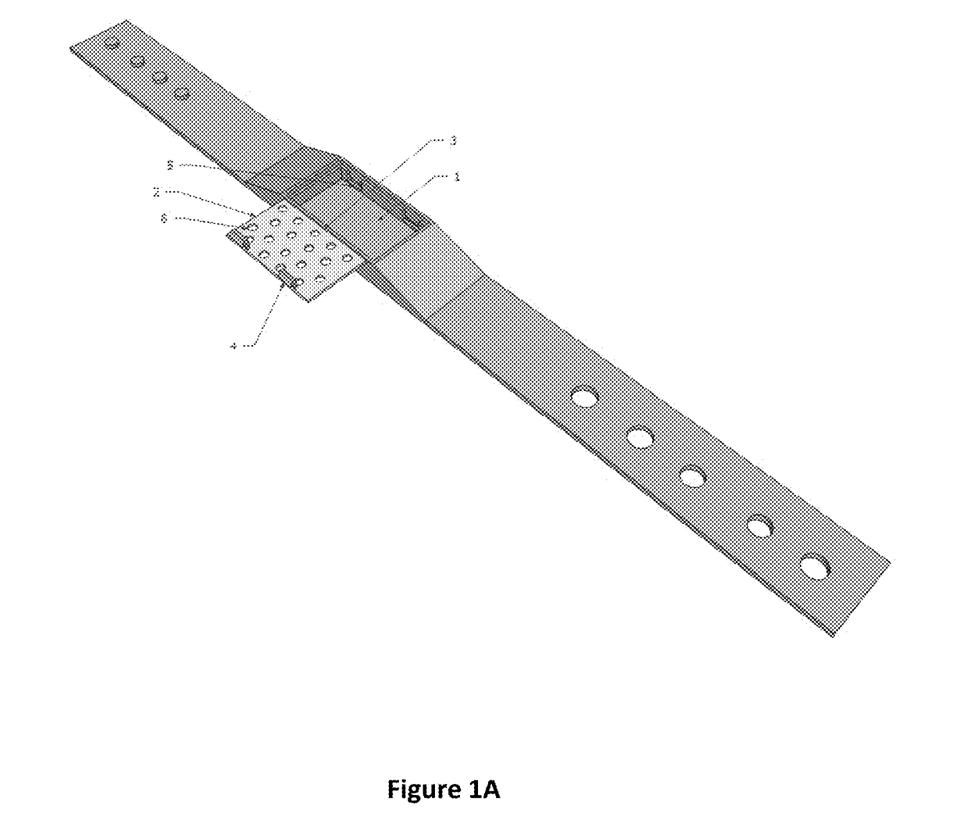
FIG. 1A is a perspective view of a wearable device for fragrance or insect repellent application.
Figure 1B:
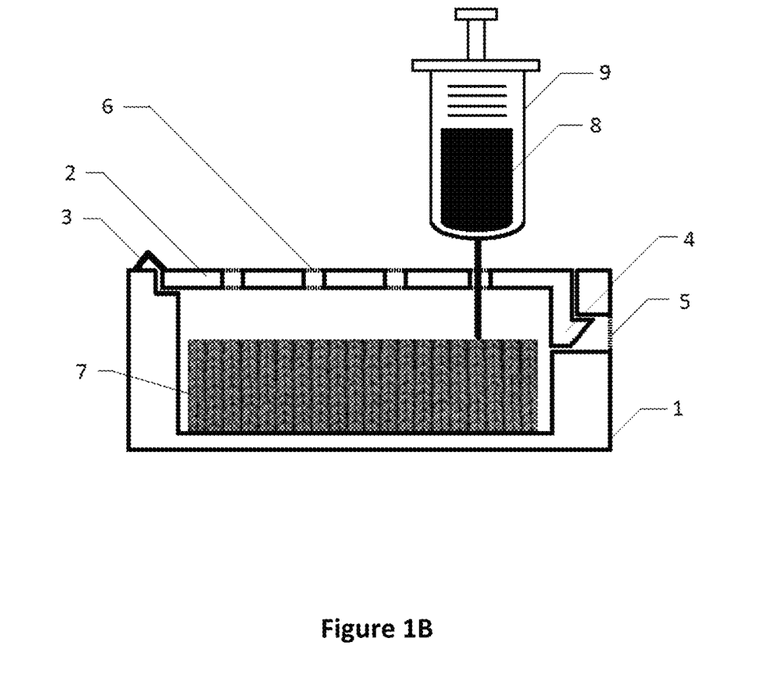
FIG. 1B is a cross section view of the wearable device of FIG. 1A being refilled.

FIGS. 1A and 1B are depictions of a wearable device for fragrance, insect repellent application, or any other appropriate aromatic. As used herein, the term "aromatic" includes any substance that is dispersed into the air, regardless of whether it is intentionally fragrant (e.g., perfume or aromatherapy oils), whether any fragrance is merely a by-product of the application (e.g., insect repellant), or whether there is no recognizable or detectable fragrance (e.g., pheromones). Regardless of whether the aromatic is fragrant, the term "aroma," as used herein, describes the substance an aromatic disperses into the air. Aromatics are commonly created by using liquids that are absorbed by an absorbing media such as cellulosic fabric or absorbing beads. Alternatively, various dried plants have been used as aromatics (e.g., potpourri) for centuries.

The container 1 is typically relatively thin, shallow, and approximately the size of a wristwatch. The container is typically composed of plastic and is connected to a covering lid 2 by a hinge-type connection 3. Inside the container 1, any suitable aromatic 7 (depicted in FIG. 1B) may be used. After the aromatic 7 is inserted into the container 1 during assembly, the arrow hook(s) 4 at the end of the covering lid 2 are locked to hole(s) 5 "permanently" on the container 1 wall.

The covering lid 2 includes holes 6 that are big enough to allow the aromatic 7 to disperse aroma into the air. The holes 6, however cannot be so big to allow the aromatic 7 to fall out of the container 1. For certain applications, the hole 6 diameter can be between 300 micrometers to 3 millimeters. The holes 6 optionally also allow users to refill the liquid ingredients 8 into the aromatic 7 inside the container 1 by using a needle syringe 9.

Figure 2:
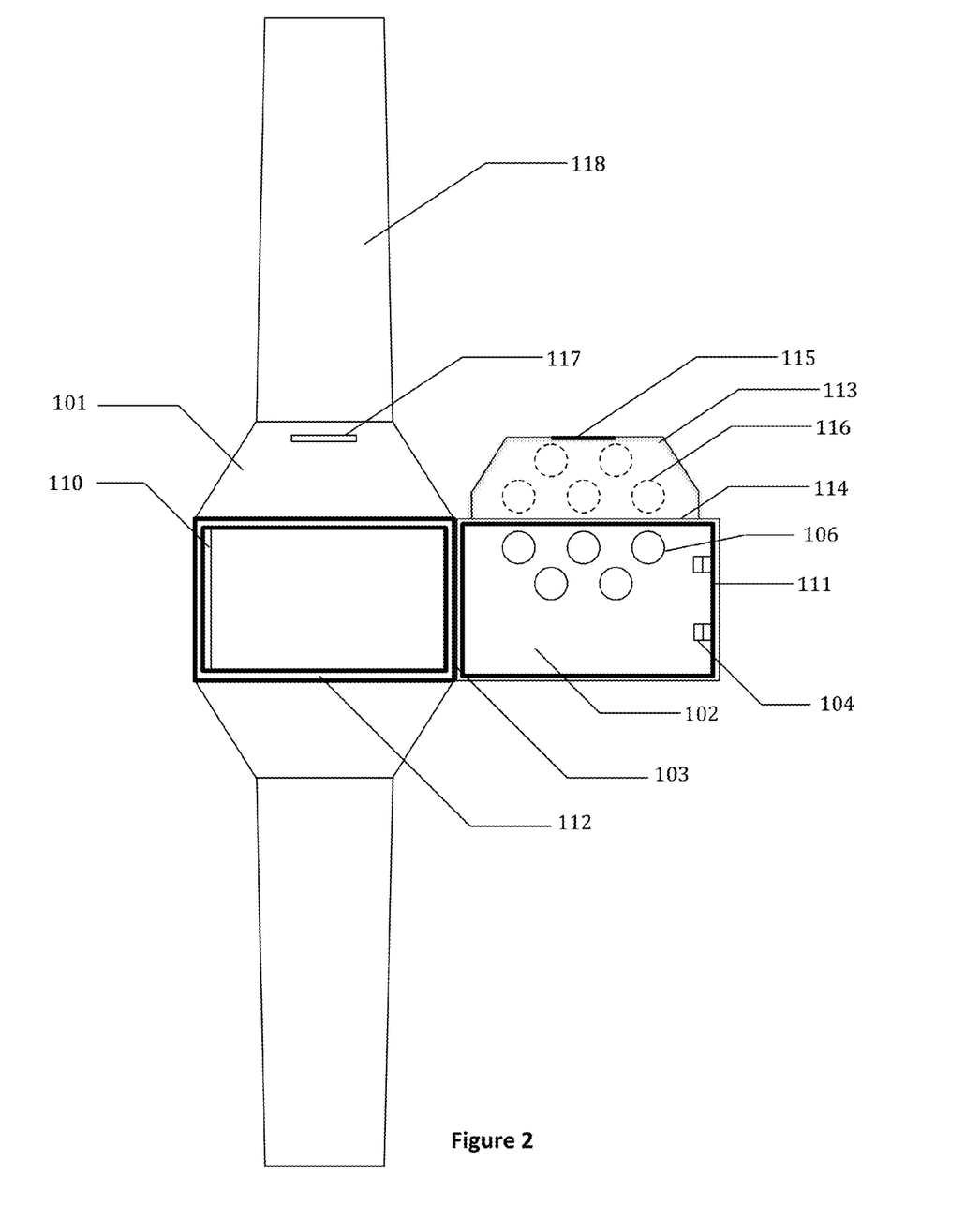
FIG. 2 is a plan view of a re-sealable wearable device for fragrance or insect repellent application.

FIG. 2 is a re-sealable wearable device for aromatics. It is similar to the device of FIGS. 1A and 1B, including a body 101, a covering lid 102, a hinge 103, arrow hook(s) 104, and holes 106 on the covering lid 102.

However, in the depicted embodiment, the covering lid 102 is engaged with the body 101 through both the arrow hook(s) 104, which locks under the ledge 110, and a lip 111, which creates a seal with the channel 112. Except for the holes 106, folding the covering lid 102 onto the body 101 preferably creates a substantially airtight seal.

A substantially airtight seal is desirable because a re-sealable lid 113 allows for the holes 106 to be sealed, creating a substantially airtight chamber for the aromatic. The re-sealable lid 113 is attached to the covering lid 102 through a hinge 114. The re-sealable lid 113 includes both a lip 115 on one side of the re-sealable lid 113 and protrusions 116 on the other side of the re-sealable lid 113.

When the covering lid 102 is engaged with the body 101, the re-sealable lid 113 can be engaged with the body 101 in two positions: "open" and "close." In the open position, the aroma from the aromatic is allowed to escape the chamber and the lip 115 of the re-sealable lid 113 is engaged in the channel 117 on the body 101. In the close position, the chamber is made substantially airtight by engaging the protrusions 116 of the re-sealable lid 113 with the holes 106 of the covering lid 102. As used herein, the phrase "substantially airtight" means the quantity of aroma released into the air (typically measured in parts-per-million or parts-per-billion) in the close position is significantly less than the quantity of aroma released into the air in the open position. In some applications, the difference between released aroma in the two positions is at least an order magnitude. The re-sealable lid 113 may be placed in either open or close position while being worn on the wrist using the wristband 118.

One advantage of the depicted embodiment is that, except for the aromatic, the entire wearable device could be made with a single injection-molded piece of thermoplastic. However, one skilled in the art could create numerous variations without undue experimentation if this advantage was not deemed important. For example, the arrow hook 104 and ledge 110 assembly could be replaced by a lock/unlock mechanism that allows for easier refilling of the aromatic by allowing the entire covering lid 102 to be opened. The re-sealable lid 113 could be a wholly separate cover that does not have a hinge 114 connecting it with the covering lid 102. The wristband 118 could be replaced with any wearable assembly, such as a belt clip, key ring or a lug hole/spring bar configuration (used for generic watch wristbands). Even if a single contiguous piece was desired, modifications could include a re-sealable lid 113 that uses latches or other non-permanent sealing mechanisms to engage with the body 101 in both the open and close positions. The holes 106 might take on any number of shapes and sizes that allow the aroma to escape while keeping the aromatic in the chamber. Further, wristband 118 could be replaced with any wearable assembly, including a belt, a pet collar, or a necklace.

Figure 3:
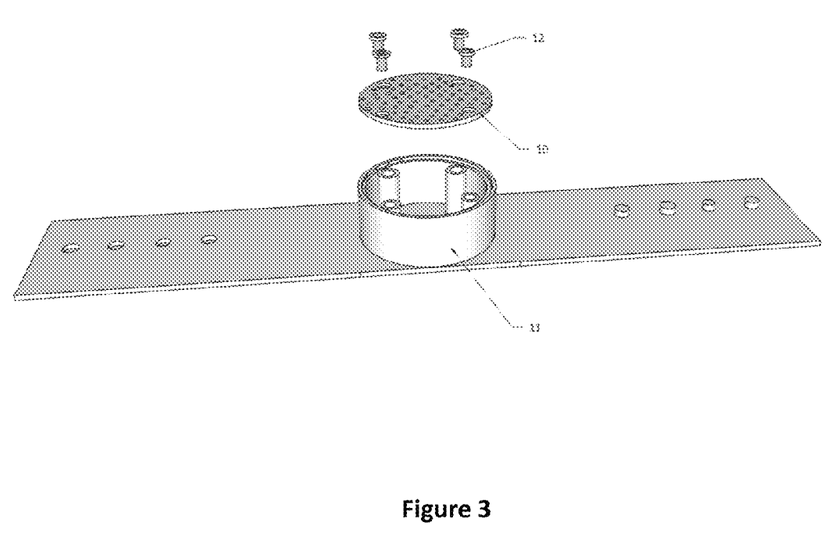
FIG. 3 is an exploded view of a child-resistant wearable device.

FIG. 3 is an exploded view of a child-resistant wearable device with the principle of child-resistance based on requiring the user to use a tool to open the cover. The principles of child-resistance of the child-resistant delivery devices includes: (a) requiring the user to use a tool, (b) requiring the user to have adult strength, (c) requiring the user to perform an alignment, and (d) requiring the user to perform two deliberate and different simultaneous motions. The covering lid 10 can be fastened to the container 11 by tightening the screws 12 with a screwdriver.

Figure 4:
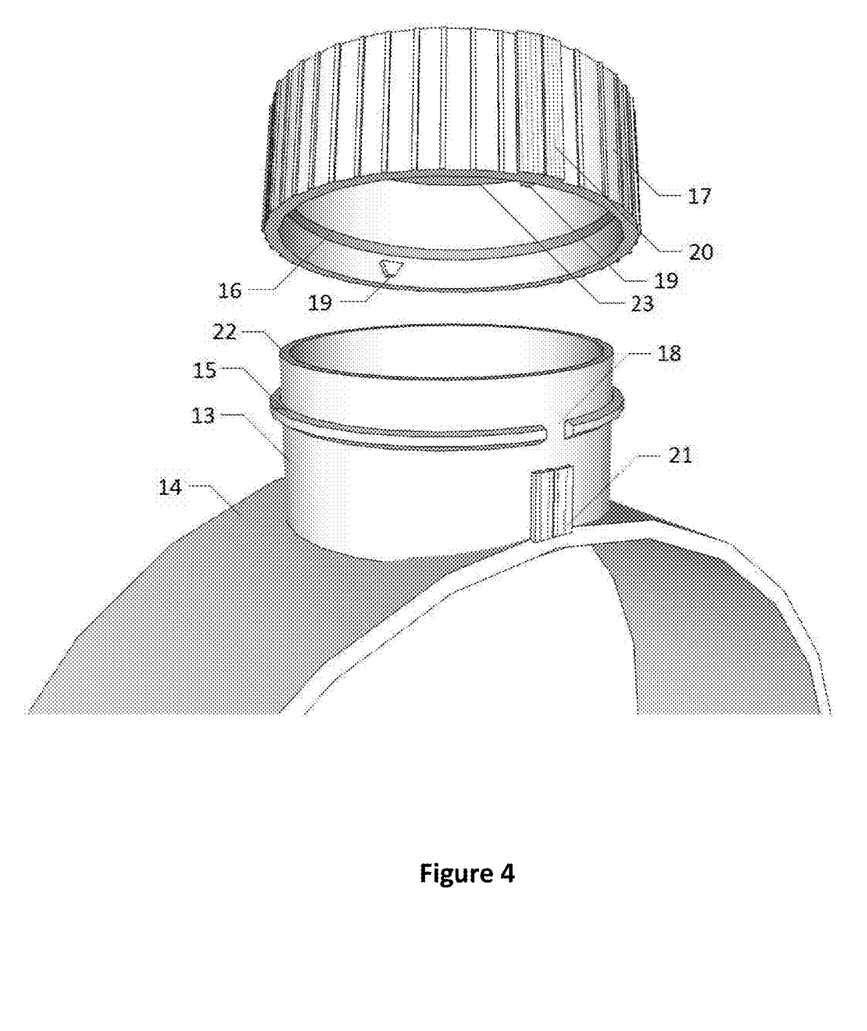
FIG. 4 is a perspective view of another embodiment of a child-resistant wearable device.

FIG. 4 is a perspective view of a child-resistant wearable device with the principle of child-resistance based on requiring the user to perform an alignment. The container is a hollow cylinder 13 mounted to a wrist strap 14. On the hollow cylinder 13, there is a lip 15 which may be mated with a corresponding indent 16 on the cap 17. There are two discontinuities 18 on the lip 15 which allow a detent 19 to pass through during cap opening and closing. The lip 15 and the container may be made of soft thermoplastics such as polyethylene or polypropylene with hardness between shore D 40 and shore D 90. The lip 15 can also function as a water resistive barrier to prevent water entering the container from outside when the cap 17 is closed. The surface of the cap 17 ribbed to increase the surface friction.

In order for the cap 17 to be closed and locked onto the container 13, the two thick ribs 20 on the cap need to be aligned with the ribs 21 on the container, so that the detent 19 is aligned with the discontinuity on the lip 18. After the alignment, the cylindrical container 13 can be pushed into the cap 17 until the edge of the container 22 touches the top wall 23 of the cap, and simultaneously the lip 15 is grasped with the mating indentation 16. The cap 17 is then turned so that the thick ribs 20 on the cap do not match with the thick ribs 21 on the container.

The locking mechanism allows the device to be child-resistant in that (A) it requires an adult strength to pull the lip 15 out of its mating indent 16, and (B) when the detent 19 is placed over the lip 15 so that the detent 19 is difficult to pass through the lip 15 at any point other than at the discontinuity 18. A similar principle but different design for child-resistant bottles is disclosed in U.S. Pat. No. 5,358, 192, which is incorporated herein by reference in its entirety for all purposes.

Figure 5:
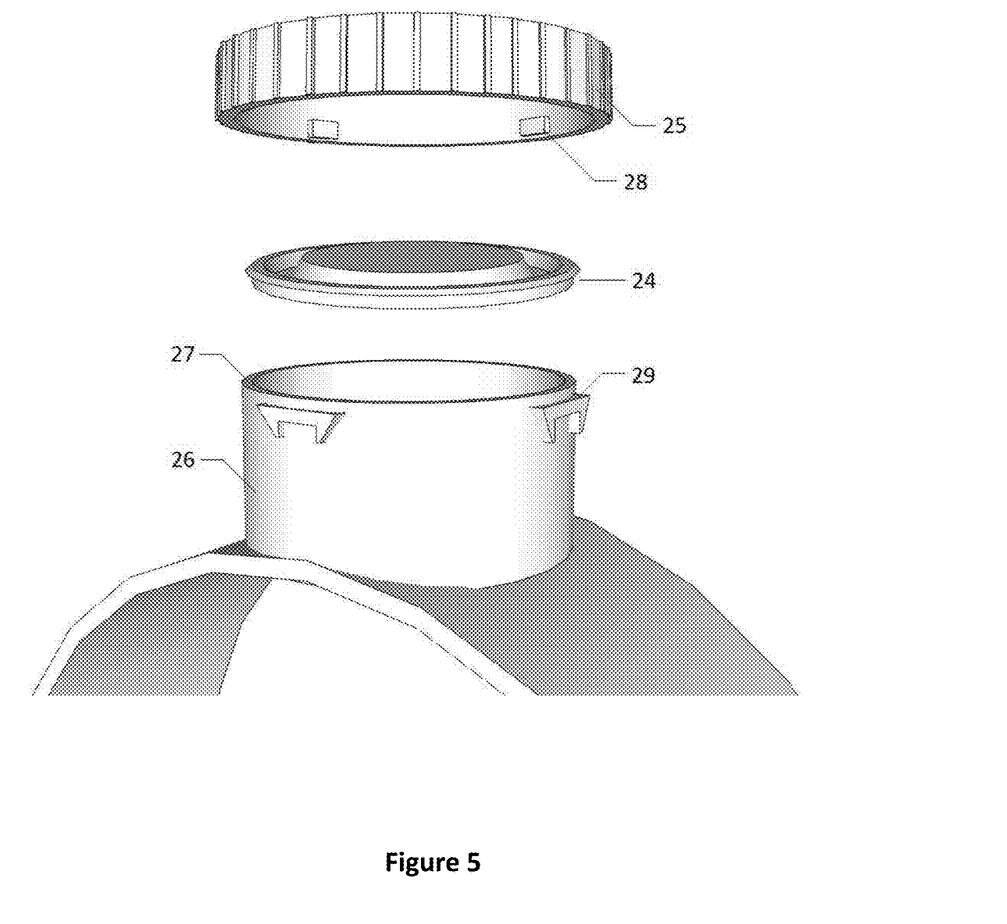
FIG. 5 is an exploded view of yet another embodiment of a child-resistant wearable device.

FIG. 5 is an exploded view of a child-resistant wearable device with the principle of child-resistance based on requiring the user to perform two deliberate and different simultaneous motions. A lining disk 24 to be inserted into the cap 25 is made of resilient thermoplastics such as Polyethylene or elastomer such as Polyurethane and silicone. The lining disk 24 can seal the container 26, to prevent materials such as medication powder escaping from the container 26, and to prevent the moisture or other contaminations entering the container 26. To close the cap 25, the user is required to push the cap 25 until the edge of the cylindrical container 27 is touching the liner disk 24, and simultaneously turn the cap 26 until the detents 28 are aligned with the double arrow shape latch brackets 29 on the container 26. Upon release from pushing, the detents 28 are locked into the latch brackets 29 by the recoiling force from the lining disk 24. To open the cap 25, the user is required to push and turn the cap 25 simultaneously.

Figure 6:
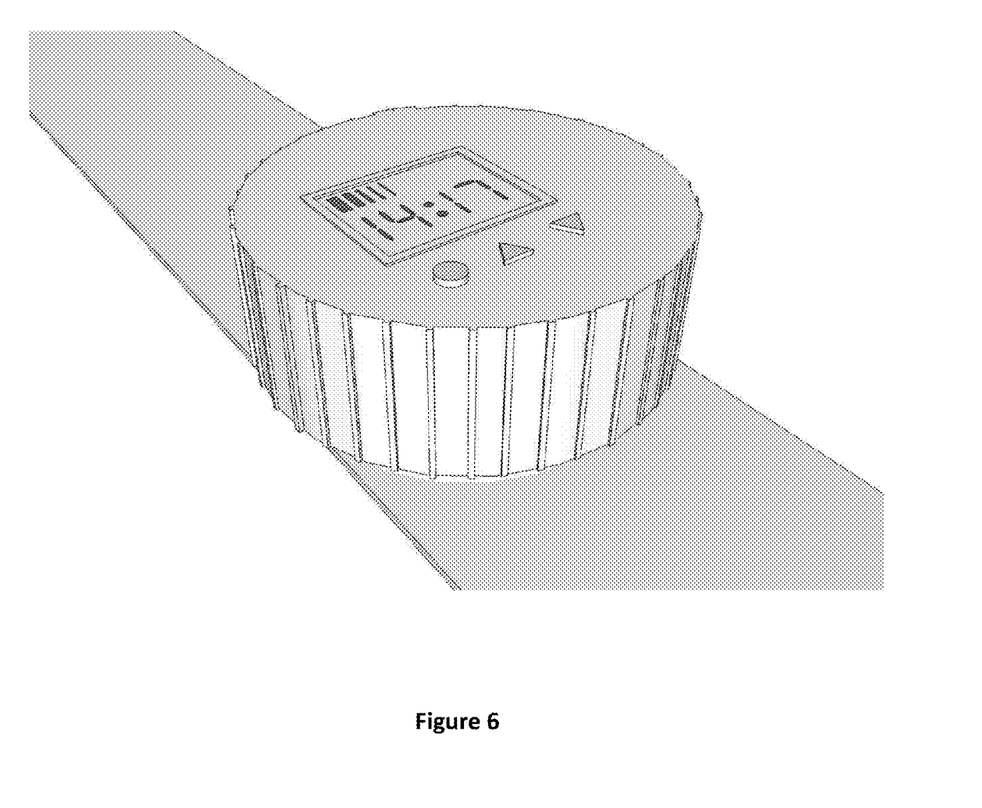
FIG. 6 is a perspective view of a wearable device equipped with an alarm clock.

A clock with an alarm function can be mounted on the cap of a child-resistant wearable device, as shown in FIG. 6. This clock device can remind the user when to take out the material such as medication from the wearable device. Both the alarm and the present time can be set by pressing the circular and triangular buttons.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed:

1. The wearable and re-sealable device for housing an aromatic that emits an aroma, comprising:
    a body that includes a chamber for housing the aromatic;
    a covering lid that engages with the body to contain the aromatic within the chamber, wherein the covering lid includes at least one hole that allows the aroma to escape from the chamber;
    a re-sealable lid that can he changeably oriented to either an open position or a close position, wherein the open position does not obstruct the at least one hole and the close position seals the at least one hole such that the chamber is airtight; and
    a wearable strap that attaches to the body;
    wherein the body, the covering lid, the re-sealable lid and the wearable strap are all constructed from a single, contiguous, piece of thermoplastic, and
    wherein the re-sealable lid engages with the body in the open position through a lip and channel assembly, whereby the lip and channel are not engaged in the close position.

2. The wearable and re-sealable device of claim 1 further comprising an absorbing media that emits an insect repellant aroma.

3. The wearable and re-sealable device of claim 1, wherein the re-sealable lid has protrusions that match the holes in the closing lid, such that the protrusions engage with the holes when the re-sealable lid is in the close position.

4. The wearable and re-sealable device of claim 1, wherein the wearable strap is a wristband.

5. The wearable and re-sealable device of claim 1, wherein the wearable strap is a pet collar.

6. The wearable and re-sealable device of claim 1, wherein the covering lid additionally engages with the body through a hook and ledge assembly.

7. The wearable and re-sealable device of claim 1, wherein the re-sealable lid is child-resistant when in the close position.

* * * * *